(12) United States Patent
Kaneko et al.

(10) Patent No.: US 10,173,013 B2
(45) Date of Patent: Jan. 8, 2019

(54) MEDICAL SYRINGE, GASKET TO BE USED FOR SYRINGE, AND GASKET PRODUCTION METHOD

(71) Applicant: SUMITOMO RUBBER INDUSTRIES, LTD., Kobe-shi, Hyogo (JP)

(72) Inventors: Hiroyuki Kaneko, Kobe (JP); Hiroaki Nakano, Kobe (JP)

(73) Assignee: SUMITOMO RUBBER INDUSTRIES, LTD., Kobe-Shi, Hyogo (JP)

(*) Notice: Subject to any disclaimer, the term of this patent is extended or adjusted under 35 U.S.C. 154(b) by 0 days.

(21) Appl. No.: 15/445,108

(22) Filed: Feb. 28, 2017

(65) Prior Publication Data

US 2017/0281873 A1 Oct. 5, 2017

(30) Foreign Application Priority Data

Mar. 30, 2016 (JP) .................... 2016-069620

(51) Int. Cl.
*A61M 5/315* (2006.01)
*A61M 5/31* (2006.01)

(52) U.S. Cl.
CPC . *A61M 5/31513* (2013.01); *A61M 2005/3101* (2013.01); *A61M 2207/00* (2013.01)

(58) Field of Classification Search
CPC ...... A61M 5/31513; A61M 2005/3101; A61M 5/31511; A61M 5/31515; A61M 2005/31516; A61M 2005/31521
See application file for complete search history.

(56) References Cited

U.S. PATENT DOCUMENTS

| | | |
|---|---|---|
| 6,090,081 A | 7/2000 | Sudo et al. |
| 2006/0178643 A1 | 8/2006 | Sudo et al. |
| 2013/0040156 A1 | 2/2013 | Nakano et al. |

(Continued)

FOREIGN PATENT DOCUMENTS

| | | |
|---|---|---|
| JP | 7-25953 Y2 | 6/1995 |
| JP | 3282322 B2 | 5/2002 |
| JP | 3387775 B2 | 3/2003 |

(Continued)

*Primary Examiner* — Theodore Stigell
*Assistant Examiner* — Hong-Van Trinh
(74) *Attorney, Agent, or Firm* — Birch, Stewart, Kolasch & Birch, LLP

(57) ABSTRACT

Laminated gasket free from liquid drug leakage. A gasket (13) for a medical syringe, with main body (14) made of elastic material, and film (15) provided on a surface of main body (14). Gasket (13) has a circumferential surface portion (17) for contact with an inner peripheral surface of a syringe barrel (11) and an annular groove (22) formed circumferentially in a surface portion of the film in the circumferential surface portion thereof. Annular groove (22) has outer edge portions (24) provided along opposite edges (23) thereof as projecting from an unprocessed surface portion of the film. Annular groove (22) has a groove formation start point and a groove formation end point connected to each other in a groove connection region. Outer edge portions (24) provided along the opposite edges of the annular groove have a maximum-to-minimum height difference of ≤5 μm in the groove connection region.

9 Claims, 7 Drawing Sheets

(56) References Cited

U.S. PATENT DOCUMENTS

2015/0148751 A1* 5/2015 Yotsutsuji ......... A61M 5/31513
                                                        604/218
2016/0287800 A1   10/2016 Nakano et al.

FOREIGN PATENT DOCUMENTS

| JP | 2003-190285 A | 7/2003 | | |
|----|---------------|--------|---|---|
| JP | 2006-181027 A | 7/2006 | | |
| JP | 4908617 B2 | 4/2012 | | |
| JP | 2014073246 A | * | 4/2014 | ........ A61M 5/31513 |
| JP | 2015-146871 A | 8/2015 | | |

* cited by examiner w (WIDTH OF OUTER EDGE PORTION)
h (HEIGHT OF OUTER EDGE PORTION)

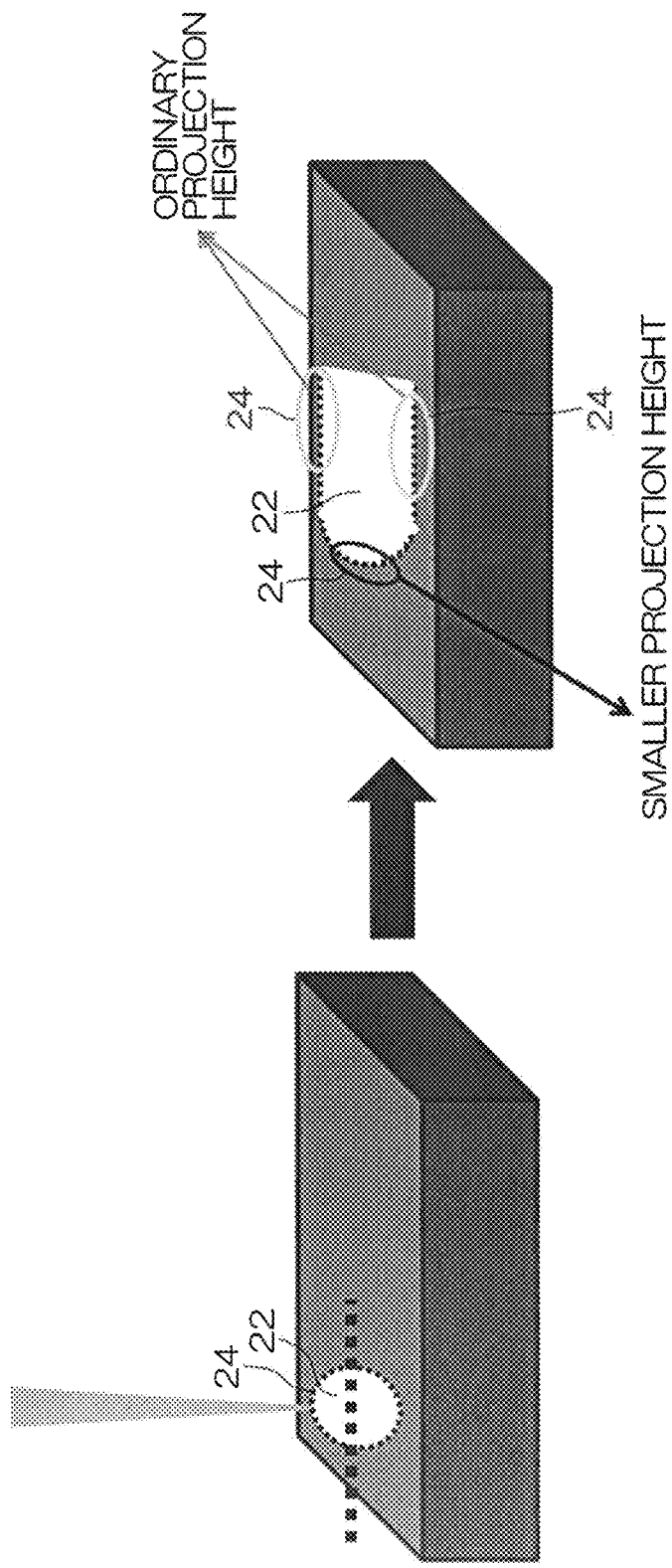
FIG. 5  ORDINARY LASER APPLICATION (AT INCIDENT ANGLE OF ZERO)

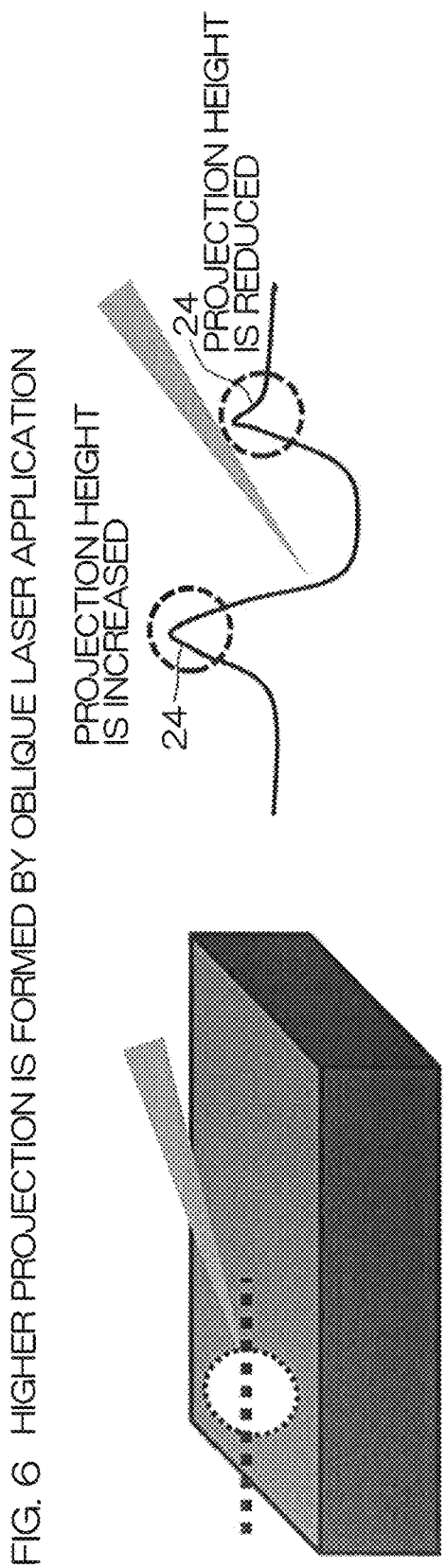
FIG. 6 HIGHER PROJECTION IS FORMED BY OBLIQUE LASER APPLICATION

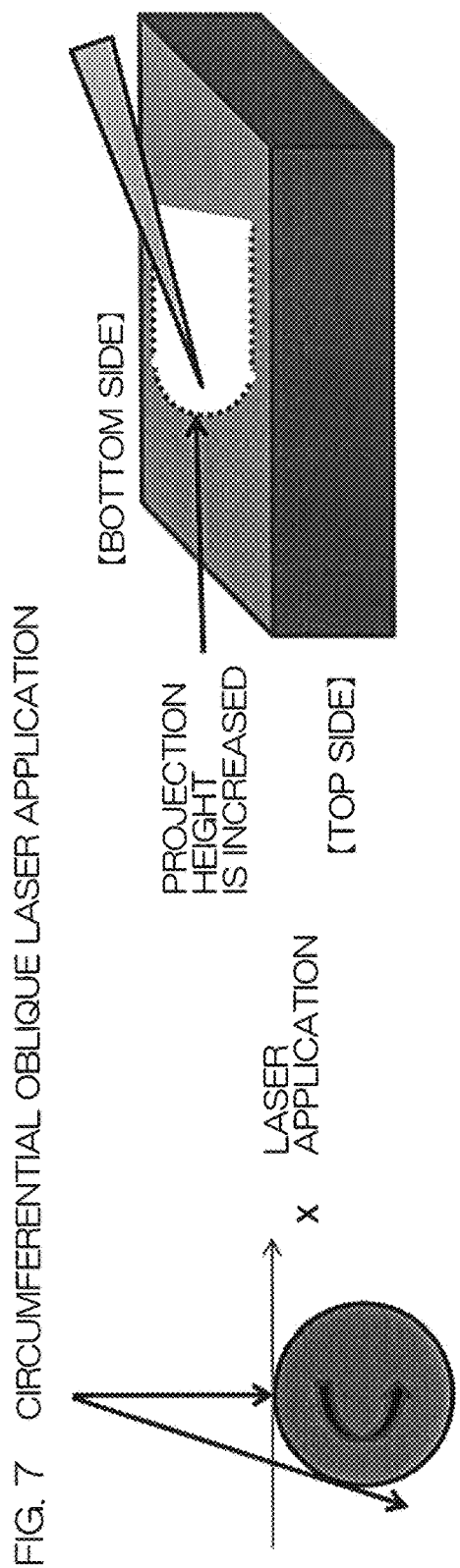

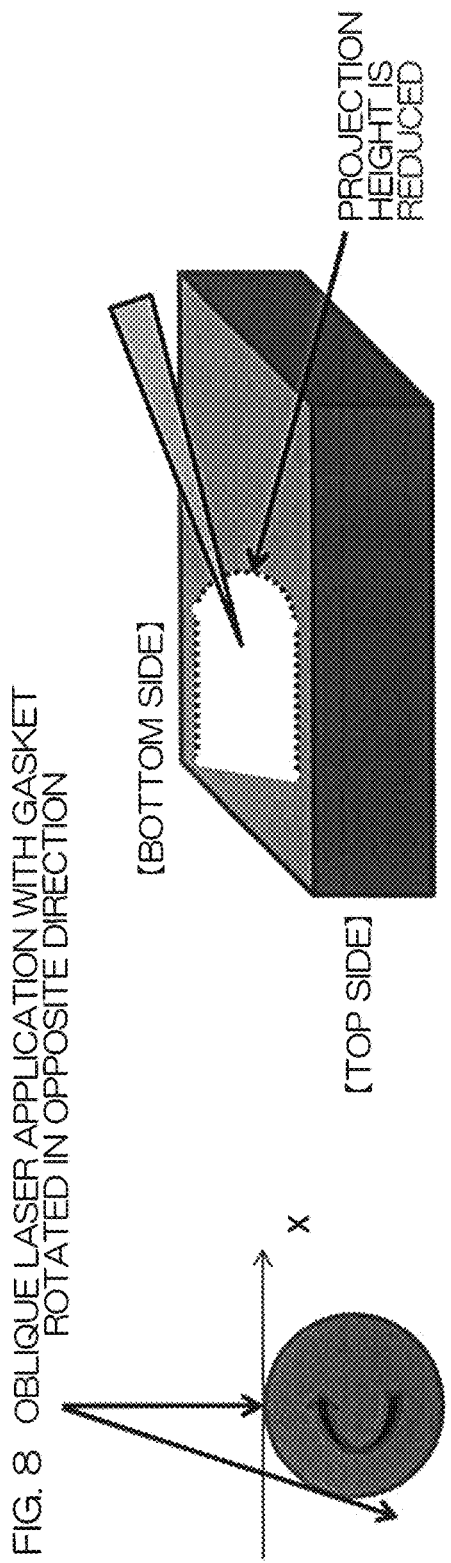
FIG. 8 OBLIQUE LASER APPLICATION WITH GASKET ROTATED IN OPPOSITE DIRECTION

MEDICAL SYRINGE, GASKET TO BE USED FOR SYRINGE, AND GASKET PRODUCTION METHOD

TECHNICAL FIELD

The present invention relates to a medical syringe, particularly to a gasket to be used for the medical syringe, and a gasket production method.

BACKGROUND ART

Syringes prefilled with a liquid drug (generally referred to as "prefilled syringes") are used as medical syringes. The prefilled syringes are advantageous because of their handling ease without the need for transferring the liquid drug into the syringe. Further, transfer of a wrong liquid drug into the syringe is advantageously prevented. Therefore, the prefilled syringes are increasingly used in recent years.

Unlike conventional syringes into which a liquid drug sucked up from a vial or other container is transferred immediately before use, the prefilled syringes are each required to serve as a container which is kept in contact with the liquid drug for a long period of time.

Such a syringe typically includes a syringe barrel, a plunger reciprocally movable in the syringe barrel, and a gasket attached to a distal end of the plunger.

The gasket to be used for the syringe is generally made of a crosslinked rubber. It is known that the crosslinked rubber contains various crosslinking components, and these crosslinking components and their thermally decomposed products are liable to migrate into the liquid drug when the liquid drug is kept in contact with the gasket. It is also known that these migrating components adversely influence the efficacy and the stability of some liquid drug.

The gasket is required to be smoothly slidable when the syringe is used. In general, the gasket made of the crosslinked rubber is poorer in slidability. To cope with this, it is a general practice to apply silicone oil to an inner surface of the syringe barrel or the surface of the gasket. However, it is also known that the silicone oil adversely influences the efficacy and the stability of some liquid drug.

From this viewpoint, a product of so-called "laminated gasket" including a rubber gasket body having a surface laminated with a highly slidable film is often used for the medical syringe. Since the surface of the rubber gasket body of the laminated gasket is covered with the highly slidable film, it is possible to prevent the components of the crosslinked rubber from migrating into the liquid drug, and to ensure the slidability even without the use of the silicone oil.

Examples of the film to be used for this purpose include ultrahigh molecular weight polyethylene films and fluororesin films which are excellent in slidability. Of these films, the fluororesin films are advantageous because of their excellent slidability and chemical stability. Of the fluororesin films, polytetrafluoroethylene (PTFE) films are particularly preferred because of their more excellent slidability and stability.

CITATION LIST

Patent Document

Patent Document 1: JP-HEI7(1995)-25953-U

SUMMARY OF THE INVENTION

Problem to be Solved by the Invention

In the laminated gasket, however, the film to be used for laminating the surface is not elastic and, therefore, is liable to impair the elasticity of the inside crosslinked rubber. The elasticity of the overall gasket is an essential requirement for reliable sealing of the liquid drug contained in the syringe barrel. If the gasket has insufficient elasticity, the liquid drug contained in the syringe barrel is liable to leak out of the syringe barrel.

The gasket needs to have a further improved slidability when being inserted into the syringe barrel.

The inventors of the present invention conducted studies to solve the aforementioned problem. As a result, the inventors found that a laminated gasket which does not contribute to leakage of the liquid drug can be provided by controlling the thickness of the film to be used for the lamination and modifying the surface of the film.

In a rubber product production process, a rubber is generally vulcanization-molded in a mold having a cavity defining a desired product shape and, after the rubber is shaped, the resulting product is demolded from the mold. In the conventional production process, when the product of the laminated gasket is demolded from the mold, the product is rubbed against the mold and, therefore, minute scratches are formed on the surface of the laminated gasket. These minute scratches are liable to prevent the reliable sealing of the liquid drug. Further, the surface is laminated with the film during the molding of the laminated gasket. Even if the mold is formed with a minute groove structure or the like, perfect transfer of the structure to the film during the molding is difficult because the film is poor in the fillability of the mold cavity (conformability and transferability).

Thus, the inventors invented a production method for a novel laminated gasket which cannot be produced by the conventional production method.

Solution to Problem

A gasket to be used for a medical syringe according to the present invention is discussed below. Further, a medical syringe according to the present invention is discussed below. Furthermore, a gasket production method according to the present invention is discussed below.

The present invention will be described below more specifically.

According to one embodiment of the invention, there is provided a gasket to be used for a medical syringe, the gasket including a main body made of an elastic material, and a film provided on a surface of the main body. The gasket has a circumferential surface portion to be brought into contact with an inner peripheral surface of a syringe barrel of the syringe, and has an annular groove formed circumferentially in a surface portion of the film present in the circumferential surface portion thereof. The annular groove has outer edge portions provided along opposite edges thereof as projecting from an unprocessed surface portion of the film. The annular groove has a groove formation start point and a groove formation end point which are connected to each other in a groove connection region. The outer edge portions provided along the opposite edges of the annular groove have a maximum-to-minimum height difference of not greater than 5 µm in the groove connection region.

In the foregoing embodiment of the invention, the groove connection region may have a circumferential length of at least 100 µm in the gasket.

According to another embodiment of the invention, there is provided a method for producing a gasket to be used for a medical syringe, the method including the steps of: molding a gasket laminated with a film and having a circumferential surface portion in a gasket molding mold; and, after demolding the gasket from the mold, forming a groove circumferentially in a portion of the film present in the circumferential surface portion of the gasket; wherein a laser processing process is performed by applying a laser beam to the circumferential surface portion of the gasket obliquely with respect to the circumferential surface portion in the groove forming step.

In this method invention, the laser beam may be applied at an incident angle of not less than 30 degrees and less than 90 degrees with respect to the circumferential surface portion of the gasket in the gasket production method.

In the foregoing method invention, the groove forming step may include the steps of setting a laser beam source so as to apply the laser beam obliquely at a predetermined incident angle with respect to the circumferential surface portion of the gasket, and rotating the circumferential surface portion of the gasket about a center axis of the gasket in a direction such that the circumferential surface portion is moved away from the laser beam obliquely applied for the formation of the groove in the gasket production method according.

In this method invention, the groove forming step may include the step of forming an annular groove in the circumferential surface portion of the gasket in the gasket production method.

According to yet another embodiment of the invention, there is provided a gasket produced by the production method described above.

According to a further embodiment of the invention, there is provided a medical syringe, which includes a tubular syringe barrel, a plunger combined with the syringe barrel and reciprocally movable in the syringe barrel, and a gasket attached to a distal end of the plunger, wherein the gasket is the gasket described above.

In this embodiment of the invention, the medical syringe may be a prefilled syringe in which the syringe barrel is prefilled with a liquid drug.

Effects of the Invention

According to the present invention, the laminated gasket for the medical syringe is excellent in sealability and slidability. The laminated gasket is particularly suitable for a prefilled syringe.

According to the present invention, the medical syringe, particularly the prefilled syringe, is excellent in sealability, and free from adverse influence on the efficacy and the stability of a liquid drug even if the syringe is kept in contact with the liquid drug for a long period of time.

According to the present invention, the gasket production method is employed for producing a laminated gasket having excellent sealability and slidability.

BRIEF DESCRIPTION OF THE DRAWINGS

FIG. 5 is a schematic diagram showing formation of a groove and outer edge portions through an ordinary laser processing process by applying a laser beam at an incident angle α of 0 degree.

FIG. 6 is a schematic diagram showing formation of outer edge portions through an oblique laser processing process by applying a laser beam obliquely at an incident angle α of 30 to 90 degrees.

FIG. 7 is a diagram showing a case in which the gasket is rotated counterclockwise and a laser beam is applied in a direction tilted leftward.

FIG. 8 is a diagram showing a case in which the gasket is rotated clockwise and a laser beam is applied in a direction tilted leftward.

DETAILED DESCRIPTION OF THE INVENTION

With reference to the attached drawings, one embodiment of the present invention will hereinafter be described specifically.

Figure 1:
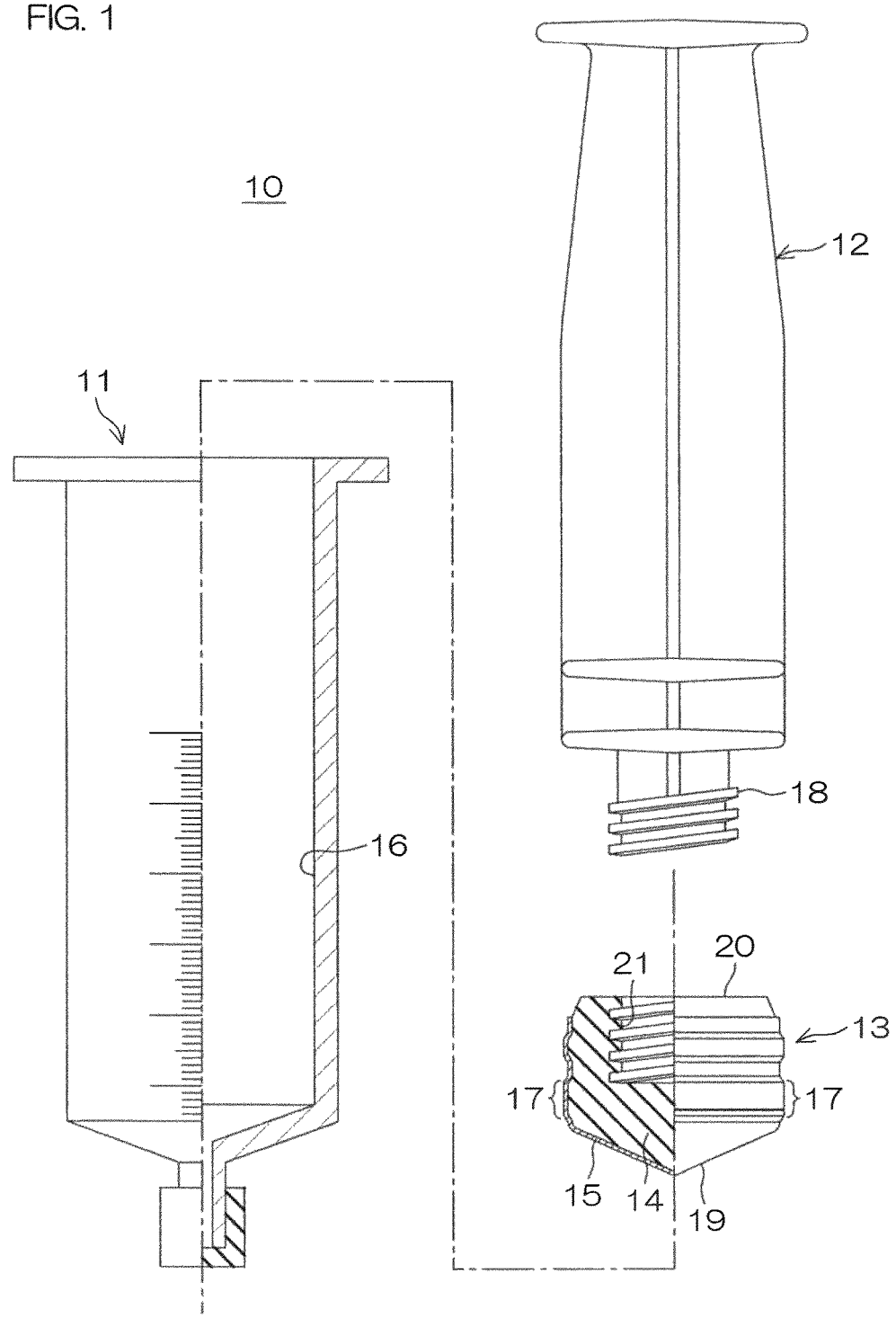
FIG. 1 is an exploded diagram illustrating a medical syringe according to an embodiment of the present invention.

FIG. 1 is an exploded diagram illustrating a medical syringe, i.e., a so-called prefilled syringe, according to the embodiment of the present invention. In FIG. 1, a half of a syringe barrel 11 and a half of a gasket 13 are illustrated in section.

Referring to FIG. 1, the prefilled syringe 10 includes a hollow cylindrical syringe barrel 11, a plunger 12 combined with the syringe barrel 11 and reciprocally movable in the syringe barrel 11, and a gasket 13 attached to a distal end of the plunger 12. The gasket 13 is a so-called laminated gasket, which includes a main body 14 made of an elastic material (a rubber or an elastomer) and a lamination film 15 provided on a surface of the main body 14. The gasket 13 has a circumferential surface portion 17 to be kept in gas-tight and liquid-tight contact with an inner peripheral surface 16 of the syringe barrel 11.

The plunger 12 includes a resin plate piece, for example, having a cross shape as seen in section, and a head 18 provided at a distal end of the resin plate piece and fitted with the gasket 13. The head 18 is an integral part of the plunger 12 made of a resin and shaped in a male screw.

The gasket 13 has a generally cylindrical shape having a short axis. The gasket 13 has a distal end face, for example, having a conical center portion projecting at an obtuse angle, and a rear end face axially recessed into an engagement recess 21 shaped in a female screw. The head 18 of the plunger 12 is screwed into the engagement recess 21 of the gasket 13, whereby the gasket 13 is attached to the distal end of the plunger 12.

Figure 2:
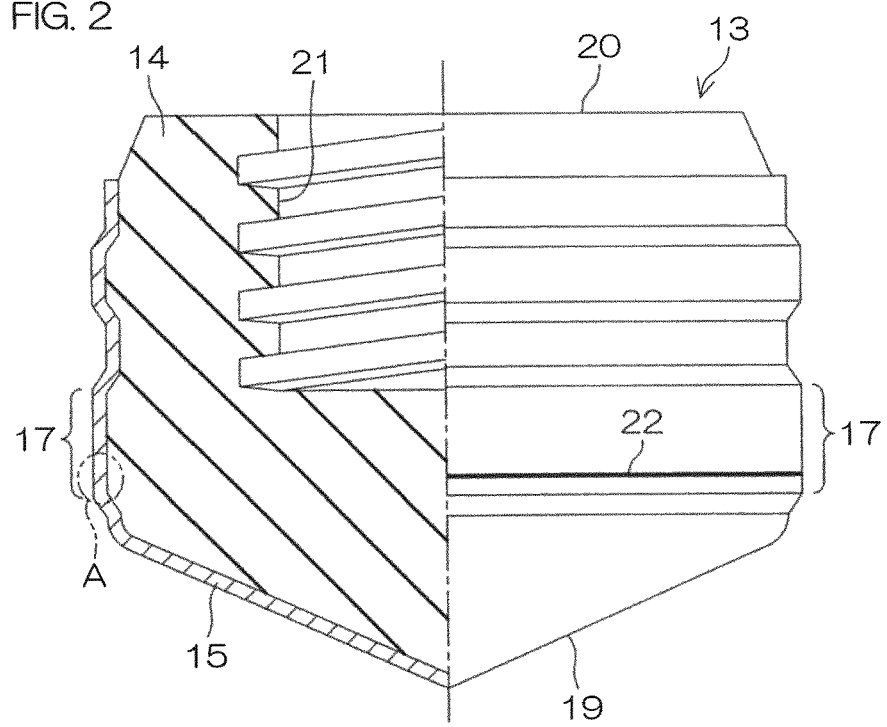
FIG. 2 is a diagram of a laminated gasket according to the embodiment of the present invention with a half of the gasket illustrated in section.

FIG. 2 is a diagram showing only the gasket 13 of FIG. 1 on an enlarged scale. In FIG. 2, a half of the gasket 13 is illustrated in section.

Referring to FIG. 2, the structure of the gasket 13 according to this embodiment will be described in greater detail.

The gasket 13 includes the main body 14, and the lamination film 15 provided on the surface of the main body 14. The main body 14 is merely required to be made of an elastic material, which is not particularly limited. Examples of the elastic material include thermosetting rubbers and thermoplastic elastomers. Particularly, the thermosetting rubbers and dynamically crosslinkable thermoplastic elastomers having crosslinking sites are more preferred because they are heat-resistant. These polymer components for the elastic material are not particularly limited, but preferred examples include ethylene-propylene-diene rubbers and butadiene rubbers which are excellent in moldability. Other preferred examples include butyl rubbers, chlorinated butyl rubbers and brominated butyl rubbers which are excellent in gas barrier property.

The type of the lamination film 15 to be provided on the surface of the main body 14 is not particularly limited, as long as the lamination film is capable of preventing migration of substances from the crosslinked rubber (main body 14) and has more excellent slidability, i.e., a smaller friction coefficient, than the rubber. Examples of the lamination film include films of ultrahigh molecular weight polyethylenes and fluororesins which are proved to be practical in medical applications. Particularly, the fluororesin films are preferred because they are excellent in slidability and have chemically stable surfaces. Usable examples of the fluororesins include conventionally known fluorine-containing resins such as PTFE, modified PTFE, ethylene tetrafluoroethylene copolymers (ETFE) and perfluoroalkyl ether (PFA). The PTFE and the modified PTFE are preferred because of their excellent slidability and chemical stability. The ETFE is also preferred because of its resistance to γ-ray to be used for sterilization. For adhesiveness to the main body 14, a film made of a mixture of these resins or a laminate film of these resins may be used.

Features of the laminated gasket 13 according to this embodiment are that the gasket 13 has the circumferential surface portion 17 to be kept in gas-tight and liquid-tight contact with the inner peripheral surface 16 of the syringe barrel 11, and that a groove 22 is formed in a surface portion of the lamination film 15 present in the circumferential surface portion 17 circumferentially of the gasket 13.

The groove 22 is an annular groove extending along the entire circumference of the circumferential surface portion 17. In this embodiment, a single groove 22 is provided by way of example.

It is merely necessary to provide at least one groove 22, and a plurality of grooves may be provided so as to be axially spaced a predetermined distance from each other. There is no need to define an upper limit in the number of the grooves.

The groove 22 is an annular groove extending circumferentially of the circumferential surface portion 17 from a start point to an end point located at the same position as the start point. With this arrangement, a liquid drug sealing effect is provided for uniformly sealing the liquid drug along the entire circumference of the circumferential surface portion 17. With the circumferential surface portion 17 of the gasket 13 being seen in a development elevation, the groove 22 preferably extends generally linearly.

Figure 3:
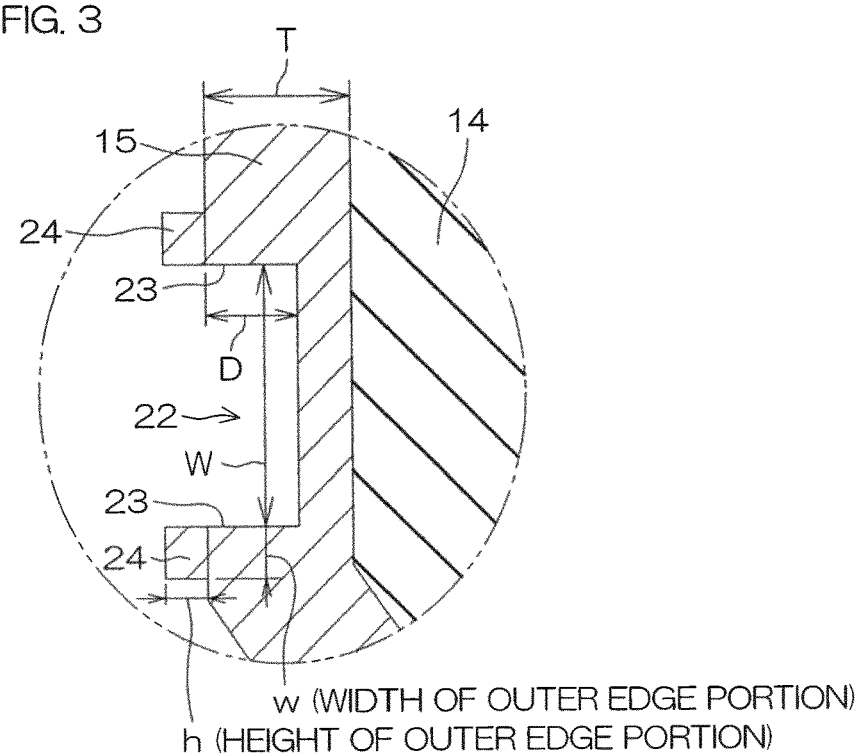
FIG. 3 is an enlarged sectional view of a portion A shown in FIG. 2.

FIG. 3 is an enlarged partial sectional view of the single groove 22 formed in the circumferential surface portion 17 of FIG. 2, i.e., an enlarged sectional view of a portion A shown in FIG. 2. Referring to FIG. 3, the groove 22 is recessed from the surface of the lamination film 15, but the main body 14 is not recessed in conformity with the groove 22. That is, the groove 22 does not influence the shape of the main body 14, but is formed only in the lamination film 15. However, the groove may be formed as having a depth greater than the thickness T of the lamination film 15 as will be described later.

The thickness T (μm) of a portion of the lamination film 15 present in the circumferential surface portion 17 of the gasket 13 is not particularly limited, but is preferably not less than 10 μm and not greater than 100 μm. If the thickness T is excessively great, the deformation conformability of the gasket 13 will be deteriorated when the gasket 13 is inserted into the syringe barrel 11. This will deteriorate the liquid drug sealability. If the thickness T is excessively small, the film is liable to be broken during the molding of the gasket 13.

The groove 22 to be formed preferably has a depth D of not less than 0.8 T (μm), more preferably not less than T (μm). The upper limit of the depth D is not particularly limited, but is preferably not greater than 1 mm for the shape stability of the gasket 13.

The width W of the groove 22 to be formed may be properly determined depending on the depth D of the groove 22 and the physical properties of the film and the rubber, but is preferably not greater than 200 μm, more preferably not greater than 150 μm, further preferably not greater than 100 μm. An excessively great width W is not preferred, because the bottom of the groove is squeezed out and deformed to be pressed against the inner surface 16 of the syringe barrel due to the elasticity of the compressed rubber when the gasket 13 is inserted into the syringe barrel. If the width W of the groove is not greater than 1 μm, on the other hand, it will be impossible to provide the desired effect because uniform formation of the groove is difficult due to the processing accuracy.

The sectional shape of the groove 22 to be formed is not particularly limited. For productivity, the groove preferably has a simply recessed sectional shape or a rounded recessed sectional shape.

The formation of the groove is achieved by cutting by irradiation with a laser beam. The laser beam is applied to the circumferential surface portion of the gasket obliquely with respect to the circumferential surface portion. More specifically, the laser beam is preferably applied to the circumferential surface portion of the gasket obliquely at an incident angle of not less than 30 degrees and less than 90 degrees, more preferably not less than 45 degrees and less than 90 degrees, further preferably not less than 60 degrees and less than 90 degrees, with respect to the circumferential surface portion. If the laser beam is applied to the circumferential surface portion at an incident angle falling outside the aforementioned range, it will be impossible to provide the intended effect such as the liquid sealability, with variations in the heights of outer edge portions in a groove connection region to be described later, when the gasket is fitted into the syringe barrel.

In general, portions of the lamination film 15 present along opposite edges 23 of the groove 22 are slightly thicker than the original thickness of the film. Where the groove 22 is formed by the processing with the laser beam, the film material is evaporated or decomposed, and partly re-deposited along the opposite edges 23 of the groove 22. Thus, outer edge portions (projections) 24 are formed along the opposite edges 23 of the groove 22.

The laminated gasket 13 is molded by means of a mold, and then demolded from the mold. At this time, the laminated gasket 13 is rubbed against the mold and, therefore, minute scratches are formed on the surface of the laminated gasket 13. However, the minute scratches are repaired by the outer edge portions (projections) 24 when the groove 22 is formed in the circumferential surface portion of the demolded laminated gasket 13. Therefore, the presence of the outer edge portions 24 along the opposite edges 23 of the groove 22 is rather preferred.

Where the groove 22 is an annular groove, the outer edge portions 24 are desirably configured so as to have a maximum-to-minimum height difference of not greater than 5 μm in a groove connection region (having a length of 100 μm) in which a groove formation start point and a groove formation end point are connected to each other. If the height difference is greater than 5 μm, it will be impossible to provide the liquid sealability when the gasket 13 is fitted in the syringe barrel 11.

The configuration of the outer edge portions 24 in a region other than the groove connection region is not particularly limited. The outer edge portions 24 preferably each have a height h of not less than 2 μm and not greater than 30 μm, more preferably not less than 4 μm and not greater than 25 μm, further preferably not less than 6 μm and not greater than 23 μm. Further, the outer edge portions 24 preferably each have a width w of not less than 2 μm and not greater than 40 μm, more preferably not less than 4 μm and not greater than 35 μm, further preferably not less than 6 μm and not greater than 30 μm.

The method of measuring the groove configuration is not particularly limited, but a laser microscope is preferably used. The depth and the width of the groove and the height and the width of the outer edge portions are measured based on an unprocessed portion of the film 15.

Next, a method for producing the gasket 13 according to this embodiment will be described.

The gasket 13 according to this embodiment is produced through the following production process steps:
(1) Molding a gasket laminated with a lamination film in a gasket molding mold; and
(2) Demolding the laminated gasket from the mold, and then forming a groove in the lamination film circumferentially of a circumferential surface portion of the gasket. The formation of the groove is achieved by a laser processing process as described above.

In the step of molding the gasket laminated with the lamination film in the mold, an unvulcanized rubber is placed on an inner surface of the lamination film in the mold, and vulcanization-molded.

For example, a sheet of an unvulcanized rubber containing a crosslinking agent is stacked on a lamination film, and vulcanization-molded in the mold. Thus, the gasket is produced as having a predetermined shape.

In this case, the inner surface of the lamination film 15 on which the rubber sheet is stacked is preferably preliminarily roughened. With the inner surface of the film 15 roughened, the rubber sheet can firmly adhere to the film 15 by the vulcanization molding without the use of an adhesive agent. The adhesion is attributable to an anchoring effect which is created with the vulcanized rubber intruding into voids formed in the roughened inner surface of the film 15.

The modification (roughening) of the inner surface of the lamination film 15 may be achieved, for example, by applying ion beam to the inner surface to break the internal molecular structure in the inner surface (see, for example, JP4908617B).

Another production method may be employed which includes the steps of applying an adhesive layer on an inner surface of a lamination film 15 not roughened, stacking an unvulcanized rubber material on the adhesive layer, and putting the resulting stack in a mold to mold the gasket in the mold.

After the gasket is molded in the mold, the groove is formed in the circumferential surface portion of the gasket. Thus, the gasket is produced as having excellent sealability.

If a production method in which the formation of the groove and the molding of the gasket are achieved simultaneously is employed, i.e., if a production method in which a groove structure is preliminarily formed in the mold and transferred to the surface of the gasket is employed, the molded gasket would be damaged or minute scratches would be formed on the molded gasket when the gasket is taken out of the mold (demolded).

Even if the minute scratches are formed during the demolding of the gasket, the minute scratches are repaired to some extent by forming the groove on the molded gasket in the subsequent groove forming step. Further, the groove formed after the molding of the gasket is advantageous for creating the desired effect.

The following laser processing process is employed for forming the groove after the molding of the gasket.

Figure 4:
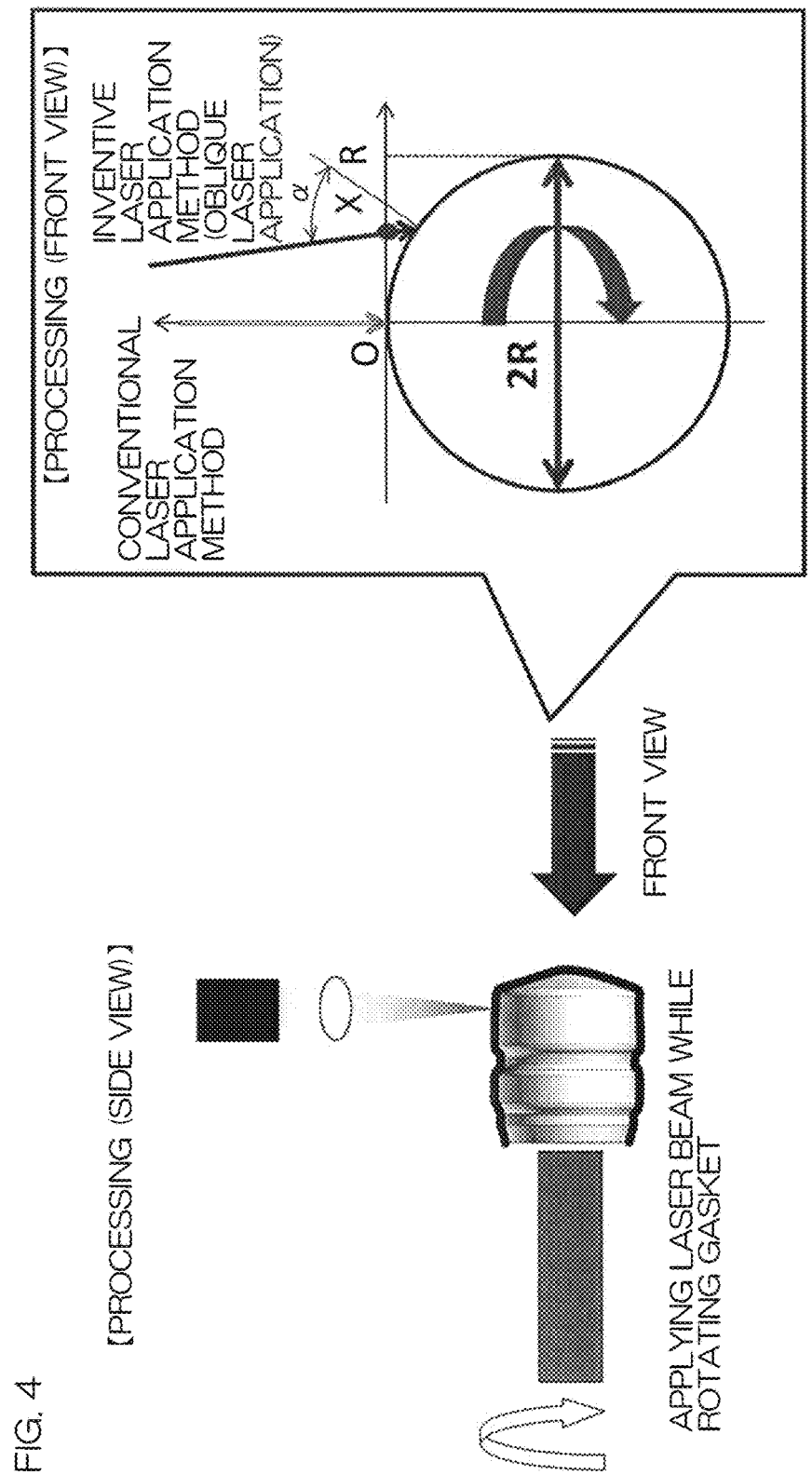
FIG. 4 is a diagram for explaining a laser processing process to be performed in the embodiment of the present invention.

FIG. 4 is a diagram for explaining the laser processing process to be performed in this embodiment. Referring to FIG. 4, the laser beam is applied obliquely to the circumferential surface portion of the gasket. At this time, the incident angle α of the laser beam with respect to the circumferential surface portion is set to 30 degrees≤α≤90 degrees.

For the formation of the annular groove in the circumferential surface portion of the gasket, a laser beam source is fixed with respect to the circumferential surface portion, and the laser beam is applied to the circumferential surface portion while the gasket is rotated about the center axis thereof. Thus, the laser beam can be applied obliquely at the predetermined incident angle α to any angular position of the circumferential surface portion, whereby the annular groove is formed uniformly.

While the laser beam is applied obliquely to the circumferential surface portion, the gasket is rotated in a rotation direction such that the circumferential surface portion is moved away from a laser beam application position at which the laser beam is obliquely applied (in FIG. 4, the gasket is rotated clockwise).

By thus performing the laser processing process, the annular groove is substantially uniformly formed in the circumferential surface portion of the gasket and, at the same time, the outer edge portions 24 are formed as intended.

Next, advantages of the oblique application of the laser beam to the circumferential surface portion will be described.

FIG. 5 is a schematic diagram showing formation of a groove 22 and outer edge portions 24 through an ordinary laser processing process by applying the laser beam at an incident angle α of 0 degree. Where the incident angle α is 0 degree, an outer edge portion 24 at a laser application start point has a relatively small height.

FIG. 6 is a schematic diagram showing formation of outer edge portions 24 through an oblique laser processing process by applying the laser beam obliquely at an incident angle α of 30 to 90 degrees. The oblique laser application process makes it possible to increase the height of an outer edge portion at a laser application start point.

Where the gasket rotation direction is such that the circumferential surface portion is moved away from the obliquely applied laser beam as shown in FIG. 7, the outer edge portion 24 at the laser application start point is relatively high in the formation of the annular groove. Therefore, when the groove is connected to the laser application start point to provide the annular groove, outer edge portions 24 are formed along the opposite edges of the annular groove as having a uniform height by advantageous function of the relatively high outer edge portion 24.

It was confirmed that, where the gasket rotation direction is such that the circumferential surface portion is moved toward the obliquely applied laser beam as shown in FIG. 8, the outer edge portions 24 have variations in height particularly in the groove connection region in the formation of the annular groove.

Where the formation of the groove is achieved by the cutting by the laser beam application, the type and the output dose of the laser beam may be properly determined based on the known art. The type of the laser beam may be properly selected according to the film material, the groove depth and the like. A laser beam processing process employing infrared radiation is preferred because of its industrial handling ease. The laser beam application period is properly selected according to the forming conditions. Particularly, application of a short pulse laser beam is preferred because the resulting heat is less liable to influence the gasket around the groove formation portion.

EXAMPLES

Two types of lamination films (a PTFE film and a modified PTFE film) were each used in combination with an unvulcanized rubber sheet, and gasket structures were produced by vulcanization-molding the rubber. Gaskets (Examples 1 to 6 and Comparative Examples 2 to 4) were each produced by forming an annular groove circumferentially in a circumferential surface portion of each of the gasket structures, and a gasket (Comparative Example 1) was produced without forming an annular groove in the gasket structure.
[Lamination Films Used]
(1) PTFE film (VALFLON (registered trade name) available from Nippon Valqua Industries, Ltd.)
(2) Modified PTFE film (VALFLON Ex1 (registered trade name) available from Nippon Valqua Industries, Ltd.)

Inner surfaces of the respective lamination films (on which the unvulcanized rubber sheet was stacked) were each preliminarily irradiated with ion beam to be thereby roughened. The films each had a thickness T as shown in Table 1.
[Main Body Material Used]
Unvulcanized rubber sheet: Halogenated butyl rubber
Crosslinking agent: 2-di-n-butylamino-4,6-dimercapto-s-triazine Zisnet DB (registered trade name) available from Sankyo Kasei Co., Ltd.
[Production Conditions]
Vulcanization temperature: 180° C.
Vulcanization period: 8 minutes
Processing pressure: 20 MPa
[Product Shape]

The gasket structures each had a gasket shape shown in FIG. 2 with a circumferential surface portion 17 thereof having a diameter of 6.60 mm.
[Formation of Groove]

A groove was formed after the gasket structures were each produced. Laser beam processing was employed for the formation of the groove.
(1) Laser Beam Processing A 3-Axis $CO_2$ Laser Marker ML-Z9550T available from Keyence Corporation was used as a laser processing apparatus.

For the processing, a laser beam having a wavelength of 9300 nm was applied with a light source of the laser processing apparatus located vertically above the top of the gasket.
[Test Method]

Measurement of Dimensions of Groove

By means of a laser microscope (VK-X100 available from Keyence Corporation), the surface geometry of each of the gasket products formed with the grooves was measured with an objective lens having a magnification of 50×. For each of the gasket products, the maximum depth and the width of the groove were measured at four positions on an image of the gasket product, and arithmetic averages were determined for the maximum depth and the width.

Liquid Drug Sealability

The gasket products thus produced were each inserted in a syringe barrel, which was in turn filled with a test liquid. Then, an opposite end of the syringe barrel was capped. The resulting syringe barrel was allowed to stand still at 40° C. for one week, and observed with an objective lens having a magnification of 50× by means of a video microscope (DVM5000 available from Leica Microsystems Inc.) to be checked for liquid leakage. For each of the gasket products, 20 samples were prepared, and the number of samples suffering from liquid leakage (in which the test liquid penetrated beyond a maximum diameter portion (circumferential surface portion 17) of the gasket product) was recorded. A gasket product with two or less samples suffering from the liquid leakage was rated as acceptable. The test liquid herein used was prepared by adding 0.2 g/liter of a colorant (Methylene Blue available from Sigma Aldrich Japan LLC.) and 1.0 g/liter of a surfactant (POLYSORBATE 80 available from NOF Corporation) to water. The syringe barrel was a glass syringe barrel (having an inner diameter of 6.35 mm).

Slidability

The processed gasket products were each inserted into the syringe barrel, and a force required for squeezing the gasket product at a speed of 100 mm/min in the syringe barrel by a plunger was measured by means of a precision universal tester (AG-X 100 kN available from Shimadzu Corporation). An average force required for sliding the gasket product for a sliding distance of 10 mm to 15 mm was determined, and recorded as a sliding resistance.

TABLE 1

|  | Example 1 | Example 2 | Example 3 | Example 4 | Example 5 | Example 6 |
| --- | --- | --- | --- | --- | --- | --- |
| Film | PTFE | PTFE | Modified PTFE | PTFE | Modified PTFE | Modified PTFE |
| Thickness T (μm) of film | 20.7 | 20.7 | 21.2 | 20.4 | 21.6 | 19.5 |
| Processing method | Laser | Laser | Laser | Laser | Laser | Laser |
| Gasket rotation direction with respect to laser application direction | Same direction | Opposite direction | Same direction | Same direction | Same direction | Same direction |
| Incident angle (degree) | 84 | 84 | 78 | 68 | 51 | 38 |

TABLE 1-continued

|  |  |  |  |  |  |  |
|---|---|---|---|---|---|---|
| Depth d (μm) of groove | 45 | 47 | 53 | 53 | 56 | 60 |
| Width (μm) of groove | 103 | 102 | 103 | 105 | 102 | 105 |
| Height (μm) of outer edge portions | 20 | 20 | 24 | 22 | 21 | 21 |
| Width (μm) of outer edge portions | 36 | 35 | 33 | 30 | 29 | 27 |
| Outer edge height difference (μm) in groove connection portion | 2 | 4 | 2 | 3 | 3 | 4 |
| Number of grooves | 4 | 4 | 2 | 1 | 4 | 4 |
| Number of gasket samples suffering from liquid leakage | 0 | 1 | 0 | 0 | 0 | 0 |
| Sliding resistance (N) | 14 | 14 | 15 | 15 | 14 | 14 |

|  | Comparative Example 1 | Comparative Example 2 | Comparative Example 3 | Comparative Example 4 |
|---|---|---|---|---|
| Film | PTFE | PTFE | PTFE | Modified PTFE |
| Thickness T (μm) of film | 20.8 | 21.1 | 19.6 | 20.9 |
| Processing method | None | Laser | Laser | Laser |
| Gasket rotation direction with respect to laser application direction | — | Same direction | Same direction | Same direction |
| Incident angle (degree) | — | 0 | 9 | 25 |
| Depth d (μm) of groove | — | 62 | 58 | 60 |
| Width (μm) of groove | — | 101 | 103 | 103 |
| Height (μm) of outer edge portions | — | 23 | 22 | 23 |
| Width (μm) of outer edge portions | — | 26 | 26 | 25 |
| Outer edge height difference (μm) in groove connection portion | — | 8 | 7.6 | 7.5 |
| Number of grooves | — | 4 | 1 | 4 |
| Number of gasket samples suffering from liquid leakage | 20 | 4 | 6 | 3 |
| Sliding resistance (N) | 18 | 14 | 15 | 14 |

[Test Results]

The gaskets of Examples 1 to 6 each having a groove or grooves formed by applying the laser beam obliquely at an angle within the predetermined angle range with respect to the circumferential surface portion each had a smaller number of samples suffering from the liquid leakage than the gaskets of Comparative Examples 1 to 4.

This application corresponds to Japanese Patent Application No. 2016-069620 filed in the Japan Patent Office on Mar. 30, 2016, the disclosure of which is incorporated herein by reference in its entirety.

What is claimed is:

1. A gasket to be used for a medical syringe, the gasket comprising:
    a main body made of an elastic material; and
    a film provided on a surface of the main body; the gasket having a circumferential surface portion to be brought into contact with an inner peripheral surface of a syringe barrel of the medical syringe, and having a cut annular groove formed circumferentially in a surface portion of the film present in the circumferential surface portion thereof;
    wherein the cut annular groove has outer edge portions provided along opposite edges thereof as projecting from an unprocessed surface portion of the film;
    wherein the cut annular groove has a groove formation start point and a groove formation end point which are connected to each other in a groove connection region, and the outer edge portions provided along the opposite edges of the cut annular groove each have a maximum-to-minimum height difference of not greater than 5 um in the groove connection region.

2. The gasket according to claim 1, wherein the cut annular groove does not influence the shape of the main body, but is formed only in the film.

3. The gasket according to claim 2, wherein a thickness T (um) of a portion of the film present in the circumferential surface portion of the gasket is not less than 10 um and not greater than 100 um.

4. The gasket according to claim 3, wherein the cut annular groove has a depth D of not less than 0.8 T (um) and not greater than 1 mm.

5. The gasket according to claim 4, wherein a width W of the cut annular groove is not greater than 200 um.

6. The gasket according to claim 1, wherein the outer edge portions each have a height h of not less than 2 μm and not greater than 30 μm.

7. The gasket according to claim 6, wherein the outer edge portions each have a width w of not less than 2 μm and not greater than 40 μm.

8. A medical syringe comprising:
    a tubular syringe barrel;
    a plunger combined with the tubular syringe barrel and reciprocally movable in the tubular syringe barrel; and
    a gasket attached to a distal end of the plunger;
    wherein the gasket is the gasket according to claim 1.

9. The medical syringe according to claim 8, which is a prefilled syringe in which the tubular syringe barrel is prefilled with a liquid drug.

* * * * *

UNITED STATES PATENT AND TRADEMARK OFFICE
CERTIFICATE OF CORRECTION

PATENT NO. : 10,173,013 B2
APPLICATION NO. : 15/445108
DATED : January 8, 2019
INVENTOR(S) : Hiroyuki Kaneko et al.

It is certified that error appears in the above-identified patent and that said Letters Patent is hereby corrected as shown below:

In the Claims

Claim 1, at Column 12, Line 30, change "um" to --µm--.

Claim 3, at Column 12, Line 36, change "(um)" to --(µm)--.

Claim 3, at Column 12, Line 37, change "um" to --µm--.

Claim 3, at Column 12, Line 38, change "um" to --µm--.

Claim 4, at Column 12, Line 40, change "(um)" to --(µm)--.

Claim 5, at Column 12, Line 43, change "um" to --µm--.

Signed and Sealed this
Ninth Day of April, 2019

Andrei Iancu
*Director of the United States Patent and Trademark Office*